(12) United States Patent
Howard et al.

(10) Patent No.: US 8,617,602 B2
(45) Date of Patent: Dec. 31, 2013

(54) IMMEDIATE RELEASE COMPOSITIONS AND METHODS FOR DELIVERING DRUG FORMULATIONS USING WEAK ACID ION EXCHANGE RESINS IN ABNORMALLY HIGH PH ENVIRONMENTS

(76) Inventors: William Wayne Howard, Morristown, NJ (US); Russell Francis Somma, Sparta, NJ (US); Sajeev Chandran, Pune, IN (US); Pravin Megharji Bhutada, Pune, IN (US); Ashish Ashokkao Deshmukh, Pune, IN (US); Hemant Hanumant Bhalerao, Pune, IN (US)

( * ) Notice: Subject to any disclaimer, the term of this patent is extended or adjusted under 35 U.S.C. 154(b) by 0 days.

(21) Appl. No.: 13/506,512

(22) Filed: Apr. 23, 2012

(65) Prior Publication Data

US 2013/0273159 A1    Oct. 17, 2013

Related U.S. Application Data

(63) Continuation-in-part of application No. 12/807,434, filed on Sep. 3, 2010, now Pat. No. 8,187,617.

(51) Int. Cl.
*A61K 9/24* (2006.01)

(52) U.S. Cl.
CPC .................................. *A61K 9/209* (2013.01)
USPC ........... 424/472; 424/400; 424/465; 424/452; 424/483

(58) Field of Classification Search
None
See application file for complete search history.

*Primary Examiner* — Bethany Barham
(74) *Attorney, Agent, or Firm* — Sheldon Kavesh

(57) ABSTRACT

Multi-layer solid oral dosage immediate release and extended release compositions and methods for delivering drug formulations using weak acid ion exchange resins in abnormally high pH environments.

9 Claims, 8 Drawing Sheets

Example 1:

IMMEDIATE RELEASE COMPOSITIONS AND METHODS FOR DELIVERING DRUG FORMULATIONS USING WEAK ACID ION EXCHANGE RESINS IN ABNORMALLY HIGH PH ENVIRONMENTS

CROSS REFERENCE TO RELATED APPLICATIONS

This application is a continuation-in-part of application Ser. No. 12/807,434 filed Sep. 3, 2010 now U.S. Pat. No. 8,187,617 and published as US 2011/006572 on Mar. 17, 2011

BACKGROUND OF THE INVENTION

The present invention relates to the use of weak acid ion exchange resins (IER) to create an immediate release (IR) drug delivery system using release enhancers to overcome the pH dependent release characteristics normally associated with weak acid resins.

Formulations containing weak acid ion exchange resins are frequently used for immediate release of pharmaceutical agents in a patient's stomach. However, release from weak acid resins is slowed and/or reduced at higher than normal stomach pH levels. High pH levels could occur if the patient is taking medications such as proton pump inhibitors (PPIs) or has a disease state that induces hypochlorhydria or achlorhydria. In either case, a weak acid formulation may not release the medicament at a rate or to an extent adequate to achieve the desired therapeutic effect.

Approximately 60 million prescriptions were written for PPIs in 2006. Additionally, in the U.S., another 10 million people were reported to have self medicated with PPIs in 2008. Furthermore, about one in three adults used antacids on a regular basis. Collectively, these statistics suggest that close to 100 million people in the U.S. could be taking a drug that could significantly interfere with the release profile of a weak acid IER formulation. The history of prior art dosage forms indicates that a serious need exists for a novel and useful solid oral dosage form that provides an unexpected advancement in the science of IER dosage forms. For example, prior art dosage forms lack the ability to provide the immediate release properties of weak acid IER formulations when administered to a patient with stomach pH environments at about 1.5 to 2.0 and above. Surprisingly and unexpectedly, weak acid resinates can be formulated to have immediate release characteristics at pH levels above about 1.5 to 2.0. The present invention creates a release enhancing weak acid resin drug formulation by adding a release enhancing agent to the formulation to increase the rate and extent of drug release from the formulation such that it meets an a priori definition of immediate release.

SUMMARY OF THE INVENTION

Surprisingly it has been found that by adding a release enhancing agent with a strong affinity for the ionic resin to a weak acid resin drug formulation, much more rapid and complete release of a resinated drug can be attained in abnormal gastric fluid than otherwise would occur without the presence of the release enhancing agent in abnormal human gastric fluid wherein the pH is much higher than normal due to the use of drugs such as PPI or the presence of disease states such as *H. pylori* or atrophic gastritis that can lead to hypochlorhydria and achlorhydria.

Thus, one can attain the rapid release properties of weak acid resinates while retaining the low sensitivity to pH change associated strong acid resins by adding a release enhancing agent to the weak acid drug formulation.

Immediate release is defined as at least 80% release of a pharmaceutically active agent within 45 minutes in a standard dissolution apparatus according to the USP 34 NF 26 section 711.

It is also desirable in many instances that a drug be released in a sustained manner over a period of about 8 hours. Both immediate release (IR) and extended release (ER) of one or more drugs may be needed. Surprisingly, it is found that that by creating an oral dosage form possessing multiple distinct layers, drug release is more rapid and more complete than if IR and ER components are mixed in a single layer.

In a first embodiment, the invention is a multi-layer solid oral dosage form pharmaceutical composition comprising:
 (i) a first distinct layer comprising:
  (a) a first pharmaceutically active agent bound to a weak acid ion exchange resin to form a weak acid ion-exchange resinate; and
  (b) a release-enhancing agent consisting of $FeCl_3$;
 (ii.) at least a second distinct layer comprising:
  (a) a drug selected from the group consisting of said first pharmaceutically active agent and a second pharmaceutically active agent, said drug being bound to a strong acid ion exchange resin to form a strong acid ion-exchange resinate; and
  (b) optionally, a coating to slow and extend release of the drug contained therein;
wherein said pharmaceutical composition is capable of immediate release of said first pharmaceutically active agent from said weak acid resinate at a pH of at least 1.5, immediate release being defined as at least 80% release of said pharmaceutically active agent within 45 minutes in a standard dissolution apparatus according to USP 34 NF 26 section 711; and wherein said release of the drug from said strong acid resinate continues over a period of at least 8 hours after ingestion.

In a second embodiment, the invention is a method of treating a patient with a stomach pH of at least about 1.5 comprising administration of a multilayer solid oral dosage form, said dosage form comprising:
 (i) a first distinct layer comprising:
  (a) a first pharmaceutically active agent bound to a weak acid ion exchange resin to form a weak acid ion-exchange resinate; and
  (b) a release-enhancing agent selected from the group consisting of an inorganic salt and an organic base;
 (ii.) at least a second distinct layer comprising:
  (a) a drug selected from the group consisting of said first pharmaceutically active agent and a second pharmaceutically active agent, said drug bound to a strong acid ion exchange resin to form a strong acid ion-exchange resinate; and
  (b) optionally, a coating to slow and extend release of the drug contained therein;
wherein said pharmaceutical composition is capable of immediate release of said first pharmaceutically active agent from said weak acid resinate at a pH of at least 1.5, immediate release being defined as at least 80% release of said pharmaceutically active agent within 45 minutes in a standard dissolution apparatus according to USP 34 NF 26 section 711; and wherein release of the drug from said strong acid resinate continues over a period of at least 8 hours after ingestion.

In a third embodiment, the invention is a method of treating a patient having a first condition and a second condition with a pharmaceutically active agent effective for treating said second condition, said method comprising the step of administering a solid oral dosage pharmaceutical composition, said solid oral dosage pharmaceutical composition comprising:
  (i) a first distinct layer comprising:
    (a) a first pharmaceutically active agent bound to a weak acid ion exchange resin to form a weak acid ion-exchange resinate; and
    (b) a release-enhancing agent selected from the group consisting of an inorganic salt and an organic base;
  (ii.) at least a second distinct layer comprising:
    (a) pharmaceutically active agent selected from the group consisting of said first pharmaceutically active agent and a second pharmaceutically active agent, said pharmaceutically active agent bound to a strong acid ion exchange resin to form a strong acid ion-exchange resinate; and
    (b) optionally, a coating to slow and extend release of the drug contained therein;
wherein said pharmaceutical composition is capable of immediate release of said first pharmaceutically active agent from said weal acid resinate at a pH of at least 1.5, immediate release being defined as at least 80% release of said pharmaceutically active agent within 45 minutes in a standard dissolution apparatus according to USP 34 NF 26 section 711; wherein release of the drug from said strong acid resinate continues over a period of at least 8 hours after ingestion; and wherein said first condition is selected from the group consisting of *Helicobacter pylori* infection, atrophic gastritis, hypochlorhydria and achlorhydria in the stomach; and wherein said second condition is a condition other than said first condition.

In a fourth embodiment, the invention is a method of treating a patient wherein the patient has within the past 24 hours been administered a compound selected from the group consisting of a proton pump inhibitor, an H2 receptor antagonist, and an antacid, said method comprising the step of administering a solid oral dosage pharmaceutical composition, said solid oral dosage pharmaceutical composition comprising:
  (i) a first distinct layer comprising:
    (a) a first pharmaceutically active agent bound to a weak acid ion exchange resin to form a weak acid ion-exchange resinate; and
    (b) a release-enhancing agent selected from the group consisting of an inorganic salt and an organic base;
  (ii.) at least a second distinct layer comprising:
    (a) pharmaceutically active agent selected from the group consisting of said first pharmaceutically active agent and a second pharmaceutically active agent, said pharmaceutically active agent bound to a strong acid ion exchange resin to form a strong acid ion-exchange resinate; and
    (b) optionally, a coating to slow and extend release of the drug contained therein;
wherein said pharmaceutical composition is capable of immediate release of said first pharmaceutically active agent from said weak acid resinate at a pH of at least 1.5, immediate release being defined as at least 80% release of said pharmaceutically active agent within 45 minutes in a standard dissolution apparatus according to USP 34 NF 26 section 711; and, wherein release of the drug from said strong acid resinate continues over a period of at least 8 hours after ingestion.

In a fifth embodiment, the invention is a method of delivering a pharmaceutically active agent to a patient, said method comprising orally administering a solid oral dosage composition comprising:
  (i) a first distinct layer comprising:
    (a) a first pharmaceutically active agent bound to a weak acid ion exchange resin to form a weak acid ion-exchange resinate; and
    (b) a release-enhancing agent selected from the group consisting of an inorganic salt and an organic base;
  (ii.) at least a second distinct layer comprising:
    (a) pharmaceutically active agent selected from the group consisting of said first pharmaceutically active agent and a second pharmaceutically active agent, said pharmaceutically active agent bound to a strong acid ion exchange resin to form a strong acid ion-exchange resinate; and,
    (b) optionally, a coating to slow and extend release of the drug contained therein;
wherein said pharmaceutical composition is capable of immediate release of said first pharmaceutically active agent from said weak acid resinate at a pH of at least 1.5, immediate release being defined as at least 80% release of said pharmaceutically active agent within 45 minutes in a standard dissolution apparatus according to USP 34 NF 26 section 711; and, wherein release of the drug from said strong acid resinate continues over a period of at least 8 hours after ingestion.

DETAILED DESCRIPTION OF THE INVENTION

Figure 1:
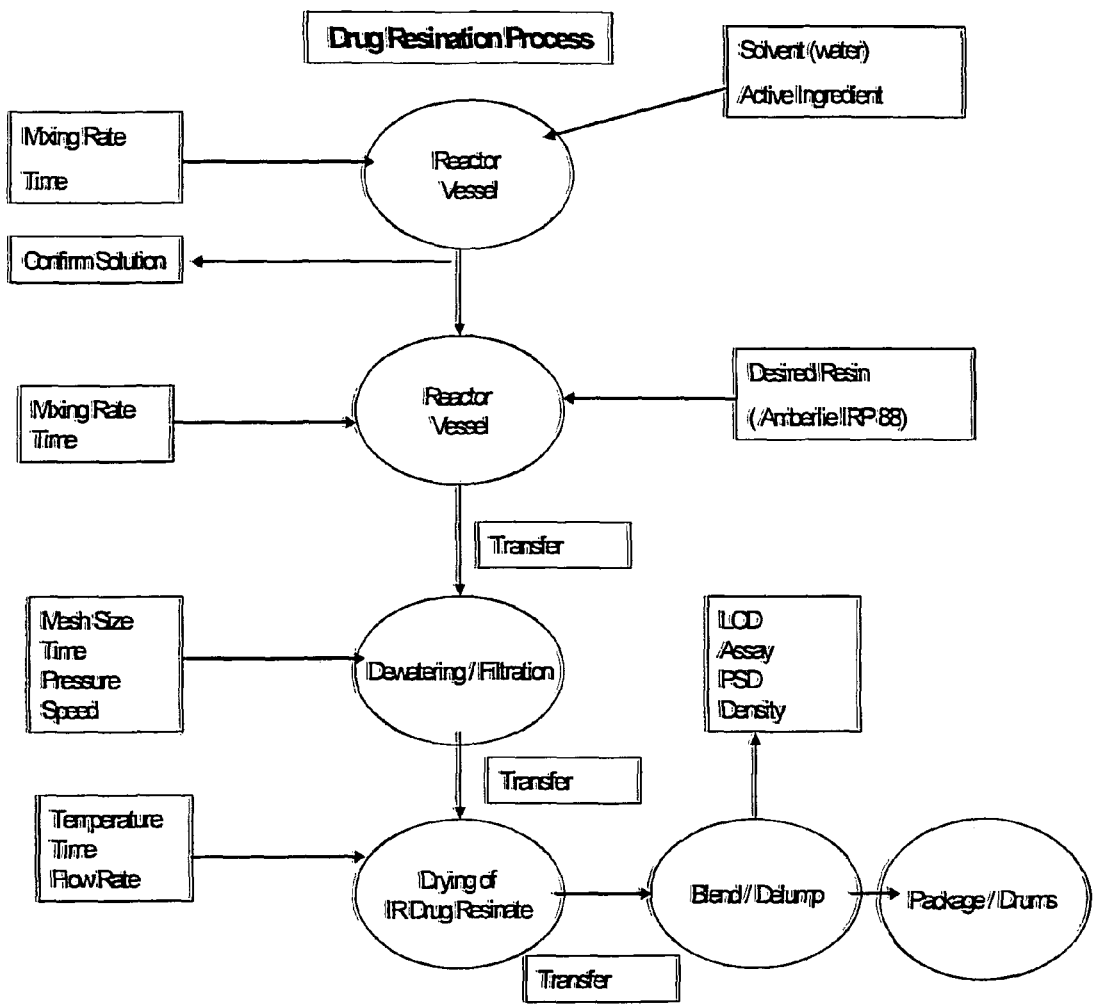
FIG. 1 is a flow chart that illustrates a process for creating a drug/resin complex, the drug resination process.

In a first embodiment, the invention is a multi-layer solid oral dosage form pharmaceutical composition comprising:
  (i) a first distinct layer comprising:
    (a) a first pharmaceutically active agent bound to a weak acid ion exchange resin to form a weak acid ion-exchange resinate, and
    (b) a release-enhancing agent consisting of $FeCl_3$;
  (ii.) at least a second distinct layer comprising:
    (a) a drug selected from the group consisting of said first pharmaceutically active agent and a second pharmaceutically active agent, said drug being bound to a strong acid ion exchange resin to form a strong acid ion-exchange resinate, and
    (b) a coating to slow and extend release of the drug contained therein;

wherein said pharmaceutical composition is capable of immediate release of said first pharmaceutically active agent from said weak acid resinate at a pH of at least 1.5, immediate release being defined as at least 80% release of said pharmaceutically active agent within 45 minutes in a standard dissolution apparatus according to USP 34 NF 26 section 711; and wherein release of the drug from said strong acid resinate continues over a period of at least 8 hours after ingestion.

The pharmaceutical compositions of the invention are characterized by faster, and/or more complete, drug release compared to a weak acid resin formulation without the release enhancing agent in pH environments at or above about 1.5 to 2.0. When administered to a patient, the release-enhancing agent results in immediate release of the pharmaceutically active agent(s) from the weak acid ion exchange resin in pH environments at or above about 1.5 to 2.0.

The pharmaceutical composition can be formulated, for example, as a multi-particle containing capsule or multiple layer compressed tablet. The immediate release component comprises a first distinct layer of the tablet or distinct particle in the capsule.

The drug release kinetics of weak acid resins can be affected by higher pH levels in the gastric fluid such that the rate and/or extent of drug release can be greatly reduced. Adding a release enhancing agent to a weak acid formulation is useful for assuring that the resinated drug is released from an IER formulation when stomach acid is reduced or eliminated (hypochlorhydria and achlorhydria) by disease states such as *Helicobacter (H.) pylori* infection or atrophic gastritis.

By adding a release enhancing agent with a strong affinity for the ionic resin to the weak acid resin drug formulation can facilitate release of the resinated drug in abnormal human gastric fluid where the pH is much higher than normal due to the use of drugs such as proton pump inhibitors or the presence of disease states such as *H. pylori* infection or atrophic gastritis.

Weak acid ion exchange resins useful in the invention include, for example, the potassium salt of carboxylated polymethacrylic resins such as Amberlite IRP88 (CAS Registry Number 39394-76-5) manufactured by Dow Chemical, and DOWEX MAC-3, manufactured by Dow Chemical but other weak acid ion exchange resins may be used.

The release-enhancing agent can be, for example, a highly soluble inorganic salt (e.g., $FeCl_3$, $FeCl_2$, $Fe_2(SO_4)_3$, $CaCl_2$, NaCl, $MgCl_2$) or an organic base (e.g., thymine, guanine, or cytosine).

The pharmaceutical composition includes at least a second distinct layer. This second layer comprises a pharmaceutical active agent bound to strong acid ion exchange resin forming a resinate and optionally coated with an extended release coating. The strong acid ion exchange resin in the second layer can be bound to the same or different pharmaceutically active agent as the weak acid ion exchange resin.

Strong acid ion exchange agents useful in the invention include sulfonated polystyrenic resins such as Amberlite IRP69, and Dowex 88, but other strong acid ion exchange resins may be used.

The coating can be any of a number of materials conventionally used such for extending drug release such as ethyl cellulose, the Eudragit™ polymers (manufactured by Degussa Rohm Pharma Polymers of Germany), Aquacoat™ (by FMC Biopolymer) and Surelease™ (by Colocon Inc.)

The weight ratio of drug to ion-exchange resin in either a weak acid or strong acid resinate can be varied to adjust a release profile. Preferably, the drug to resin weight ratio in a resinate is from about 1:0.5 to about 1:10. More preferably, the drug to resin weight ratio in a resinate is from about 1:0.75 to about 1:5. Most preferably, the drug to resin weight ratio in a resinate is from about 1:1 to about 1:3.

The weight ratio of drug in the IR layer to the drug in the ER layer can also be varied to adjust a release profile. The weight ratio of IR drug to ER drug is preferably from about 10:90 to about 90:10. More preferably, the weight ratio of IR drug to ER drug is from about 20:80 to about 80:20; yet more preferably from about 30:70 to about 70:30; and most preferably from about 40:60 to about 60:40.

By "release-enhancing agent" is meant an agent that, when added to a drug resin formulation, increases the rate and/or the extent of drug release than would otherwise occur without the release-enhancing agent in the same formulation.

By "pharmaceutically active agent" is meant agents other than food articles that are intended to diagnose, cure, mitigate, treat or prevent disease in man or other animals or that are intended to affect the structure or any function of the body of man or other animals that are physiologically acceptable. The agent could be a combination of drug therapies as well as a single agent.

By "physiologically acceptable" is meant those substances that are adequately tolerated without causing unacceptable negative side effects.

By "ion exchange resin" is meant an insoluble solid matrix that carries exchangeable ions with either a positive or negative charge. The trapping of ions takes place only with simultaneous releasing of other ions. Ions are exchanged in stoichiometrically equivalent amounts of other ions with the same electrical charge when the ion exchange material is in contact with an electrolyte solution.

By "resinate" is meant the complex formed when a drug exchanges an ion with a resin particle in the stoichiometric process described above and a drug/resin compound is formed.

By "weak acid ion exchange resin" is meant in a weak acid resin the ionizable group introduced to the polymer is a carboxylic acid (COOH) as opposed to the sulfonic acid group ($SO_3H$) used in strong acid resins. These resins behave similarly to weak organic acids so are weakly dissociated i.e. have fewer ions available for exchange.

By "immediate release" (IR) is meant that the pharmacologically active agent is released from the IR portion of the formulation such that 80%, 85%, 90%, or even 95% of the pharmaceutically active agent in the IR portion is released within 45 minutes when dissolution is measured according to the USP 34 NF 26 section 711.

By "extended release" is meant that the pharmaceutically active agent is released from the formulation at a controlled rate such that the formulation allows for a reduction in dosing frequency as compared to that presented by a conventional dosage form, e.g. an immediate release dosage form.

Release-Enhancing Agents

The drug-containing weak acid ion exchange resins of the invention are formulated with release-enhancing agents. These release-enhancing agents result in immediate release of the drug from the weak acid ion exchange resins in pH environments at or above 2.0. Examples of suitable release-enhancing agents are:

Inorganic Agents:
$FeCl_3$, $Fe_2(SO_4)_3$
$CaCl_2$
$MgCl_2$
$FeCl_2$
Organic Agents:
Thymine
Guanine
Cytosine Pharmaceutically Active Agents The invention features methods and compositions for immediate release of pharmaceutically active agents using a weak acid ion exchange resin. Examples of such pharmaceutically active agents suitable for the compounds and methods of the inventions are:

A: Anti-tussives, e.g., benzonatate, caramiphen edisylate, chlophedianol, codeine, dextromethorphan hydrobromide, hydrocodone, levopropoxyphene, morphine codeine, ethylmorphine, dihydrocodeine, benzylmorphine, laudanum, dihydroisocodeine, nicocodeine, nicodicodeine, hydrocodone, hydromorphone, acetyldihydrocodeine, thebacon, diamorphine (heroin), acetylmorphone, noscapine, and pholcodine.

B: Narcotic analgesics, e.g., codeine, oxycodone, hydrocodone, diamorphine, pethidine, morphine, oxymorphone, nalorphine, naloxone, naltrexone, opium, hydromorphone, nicomorphine, dihydrocodeine, and papavereturn.

C: Decongestants, e.g., pseudoephedrine hydrochloride, phenylephrine bitartrate, phenylephrine hydrochloride and pseudoephedrine sulfate.

D: Non-steroidal anti-inflammatory drugs, e.g., aspirin, magnesium salicylate, diclofenac, etodolac, indometacin, nabumetone, sulindac, tolmetin, ibuprofen, ketoprofen, mefenamic acid, meclofenamic acid, phenylbutazone, piroxicam, meloxicam, celecoxib, parecoxib, rofecoxib, valdecoxib, and naproxen sodium.

E: Anti-emetic drugs, e.g., dolasetron, granisetron, ondansetron, tropisetron, palonosetron, mirtazapine, metoclopramide, cyclizine, diphenhydramine, dimenhydrinate, meclizine, promethazine, and hydroxyzine.

F: Anti-histamines, e.g., diphenhydramine, loratadine, desloratadine, meclizine, fexofenadine, pheniramine, cetirizine, promethazine, brompheniramine, clemastine fumarate and chlorpheniramine.

G: Proton pump inhibitors (PPI), e.g., omeprazole, esomeprazole, pantoprazole, lansoprazole, and rabeprazole.

H: H2 Antagonists, e.g., cimetidine, ranitidine, and famotidine.

I: Anti-depressants, e.g., citalopram, escitalopram, fluoxetine, fluvoxamine, paroxetine, sertraline, desvenlafaxine, duloxetine, milnacipran, venlafaxine, atomoxetine, mazindol, reboxetine, viloxazine, amitriptyline, clomipramine, doxepin, imipramine, trimipramine, desipramine, nortriptyline, protriptyline, moclobemide, phenelzine, and selegiline.

J: Tranquilizers, e.g., amobarbital, pentobarbital, secobarbital, phenobarbital, clonazepam, diazepam, estazolam, flunitrazepam, lorazepam, midazolam, nitrazepam, oxazepam, triazolam, temazepam, chlordiazepoxide, and alprazolam.

K: Anti-convulsants, e.g., felbamate, carbamazepine, oxcarbazepine, vigabatrin, progabide, tiagabine, topiramate, gabapentin, pregabalin, ethotoin, and phenytoin.

L: Hypnotics, e.g., zolpidem, zaleplon, zopiclone, and eszopiclone.

M: Muscle relaxants, e.g., methocarbamol, carisoprodol, chlorzoxazone, cyclobenzaprine, gabapentin, metaxalone, and orphenadrine.

N: Anti-psychotics, e.g., haloperidol, droperidol, chlorpromazine, fluphenazine, perphenazine, prochlorperazine, thioridazine, trifluoperazine, mesoridazine, promazine, triflupromazine, levomepromazine, methotrimeprazine, pimozide, chlorprothixene, flupenthixol, thiothixene, zuclopenthixol, clozapine, olanzapine, risperidone, quetiapine, ziprasidone, amisulpride, asenapine, and paliperidone.

O: Anti-microbials, e.g., EDTA, zinc compounds, triclosan, domiphen, cetyl pyridium chloride, domiphen bromide, fluorides, alexidine, and octenidine.

P: Anti-diarrheals, e.g., bismuth subsalicylate and loperamide.

R: CNS stimulants, e.g., caffeine, cocaine, and amphetamines.

S: Attention Deficit and Hyperactivity Disorder drugs, e.g., methylphenidate, dextroamphetamine sulfate, amphetamine, and atomoxetine hydrochloride.

The invention also includes methods and compositions for delivering combinations of pharmaceutically active compounds. Examples of such combinations are:

A: an anti-tussive and an antihistamine
B: an anti-tussive and a decongestant
C: an anti-tussive and an analgesic
D: an anti-tussive and an NSAID
E: an anti-tussive and an antihistamine and a decongestant
F: an anti-tussive and an antihistamine and an analgesic
G: an anti-tussive and an antihistamine and an NSAID
H: an anti-tussive and an antihistamine and a decongestant and an analgesic
I: a muscle relaxant and an analgesic
J: a muscle relaxant and an NSAID
K: a muscle relaxant and an analgesic and an NSAID
L: a PPI and an NSAID
M: an H2 antagonist and an NSAID
N: a PPI and an analgesic
O: an H2 antagonist and an analgesic Dosage Forms Suitable dosage forms include a multi-particle containing capsule or multiple layer compressed tablet. The immediate release component comprises a first distinct layer of the tablet or distinct particle in the capsule.

In a second embodiment, the invention is a method of treating a patient with a stomach pH of at least about 1.5 comprising administration of a multilayer solid oral dosage form, said dosage form comprising:
(i) a first distinct layer comprising:
  (a) a first pharmaceutically active agent bound to a weak acid ion exchange resin to form a weak acid ion-exchange resinate; and
  (b) a release-enhancing agent selected from the group consisting of an inorganic salt and an organic base;
(ii.) at least a second distinct layer comprising:
  (a) a drug selected from the group consisting of said first pharmaceutically active agent and a second pharmaceutically active agent, said drug bound to a strong acid ion exchange resin to form a strong acid ion-exchange resinate; and
  (b) optionally, a coating to slow and extend release of the drug contained therein;
wherein said pharmaceutical composition is capable of immediate release of said first pharmaceutically active agent from said weak acid resinate at a pH of at least 1.5, immediate release being defined as at least 80% release of said pharmaceutically active agent within 45 minutes in a standard dissolution apparatus according to USP 34 NF 26 section 711; and wherein release of the drug from said strong acid resinate continues over a period of at least 8 hours after ingestion.

In a third embodiment, the invention is a method of treating a patient having a first condition and a second condition with a pharmaceutically active agent effective for treating said second condition, said method comprising the step of administering a solid oral dosage pharmaceutical composition, said solid oral dosage pharmaceutical composition comprising:
(i) a first distinct layer comprising:
  (a) a first pharmaceutically active agent bound to a weak acid ion exchange resin to form a weak acid ion-exchange resinate; and (b) a release-enhancing agent selected from the group consisting of an inorganic salt and an organic base;
(ii.) at least a second distinct layer comprising:
(a) pharmaceutically active agent selected from the group consisting of said first pharmaceutically active agent and a second pharmaceutically active agent, said pharmaceutically active agent bound to a strong acid ion exchange resin to form a strong acid ion-exchange resinate; and
(b) optionally, a coating to slow and extend release of the drug contained therein;
wherein said pharmaceutical composition is capable of immediate release of said first pharmaceutically active agent from said weal acid resinate at a pH of at least 1.5, immediate release being defined as at least 80% release of said pharmaceutically active agent within 45 minutes in a standard dissolution apparatus according to USP 34 NF 26 section 711;
wherein release of the drug from said strong acid resinate continues over a period of at least 8 hours after ingestion; and
wherein said first condition is selected from the group consisting of *Helicobacter pylori* infection, atrophic gastritis, hypochlorhydria and achlorhydria in the stomach; and
wherein said second condition is a condition other than said first condition.

In a fourth embodiment, the invention is a method of treating a patient wherein the patient has within the past 24 hours been administered a compound selected from the group consisting of a proton pump inhibitor, an H2 receptor antagonist, and an antacid, said method comprising the step of administering a solid oral dosage pharmaceutical composition, said solid oral dosage pharmaceutical composition comprising:
(i) a first distinct layer comprising:
(a) a first pharmaceutically active agent bound to a weak acid ion exchange resin to form a weak acid ion-exchange resinate; and
(b) a release-enhancing agent selected from the group consisting of an inorganic salt and an organic base;
(ii.) at least a second distinct layer comprising:
(a) pharmaceutically active agent selected from the group consisting of said first pharmaceutically active agent and a second pharmaceutically active agent, said pharmaceutically active agent bound to a strong acid ion exchange resin to form a strong acid ion-exchange resinate; and
(b) optionally, a coating to slow and extend release of the drug contained therein;
wherein said pharmaceutical composition is capable of immediate release of said first pharmaceutically active agent from said weak acid resinate at a pH of at least 1.5, immediate release being defined as at least 80% release of said pharmaceutically active agent within 45 minutes in a standard dissolution apparatus according to USP 34 NF 26 section 711; and,
wherein release of the drug from said strong acid resinate continues over a period of at least 8 hours after ingestion.

In a fifth embodiment, the invention is a method of delivery a pharmaceutically active agent to a patient, said method comprising orally administering a solid oral dosage composition comprising:
(i) a first distinct layer comprising:
(a) a first pharmaceutically active agent bound to a weak acid ion exchange resin to form a weak acid ion-exchange resinate; and
(b) a release-enhancing agent selected from the group consisting of an inorganic salt and an organic base;
(ii.) at least a second distinct layer comprising:
(a) pharmaceutically active agent selected from the group consisting of said first pharmaceutically active agent and a second pharmaceutically active agent, said pharmaceutically active agent bound to a strong acid ion exchange resin to form a strong acid ion-exchange resinate; and,
(b) optionally, a coating to slow and extend release of the drug contained therein;
wherein said pharmaceutical composition is capable of immediate release of said first pharmaceutically active agent from said weak acid resinate at a pH of at least 1.5, immediate release being defined as at least 80% release of said pharmaceutically active agent within 45 minutes in a standard dissolution apparatus according to USP 34 NF 26 section 711; and,
wherein release of the drug from said strong acid resinate continues over a period of at least 8 hours after ingestion.

EXAMPLES

Each of the compositions of the examples below are useful for oral administration for conditions such as normal stomach pH of about 1.5 to 2.0 or higher, *Helicobacter pylori* infection, atrophic gastritis, hypochlorhydria and achlorhydria. The compositions of the examples are also useful for patients who have been administered a proton pump inhibitor, or a H2 receptor antagonist or an antacid within the preceding 24 hours.

Example 1

Example of a Process for Creating a Drug/Resin Complex 500 mg of Amberlite IRP88™, the potassium salt of carboxylated polymethacrylic ion-exchange resin from Rohm and Haas (currently DOW), were added to deionized water (2.5 L) which had been heated to 85° C. The resin and water were mixed using a magnetic stirring bar until a uniform suspension was obtained. 150 mg of hydrocodone bitartrate was made into a solution in deionized water and then added to the resin slurry and mixed in the primary vessel with continued mixing for 4.0 hours at 85° C. to create the hydrocodone resinate. The slurry was vacuum filtered to separate the resinate from the water. The resin particles were washed three times by re-suspending the particles in 5 liters of deionized water maintained at 85° C. The resulting washed particles were filtered and allowed to cool for 12 hours. This process was repeated in order to generate adequate amounts of the hydrocodone resinate to prepare the number of capsules required for dissolution testing. Care was taken during the cooling process to avoid cake formation by periodically mixing the resinate bed with a glass stirring rod. The resinate was then dried using a lab scale fluid bed dryer set at 55° C. inlet temperature. Drying was continued until a residual moisture content of 2.0% was obtained. Drug loading was tested and showed approximately 40% drug load or approximately 40 mg of hydrocodone per 100 mg of resinate.

FIG. 1 is an illustration of the process for creating the resinate. A similar procedure is followed for forming a drug resinate of a strong acid ion-exchange resin such as a sulfonate polistirex resin such as IRP69.

Example 2

The Effect of a Release Enhancer on a Weak Acid Resinate

A resinate was prepared by reacting codeine with a weak acid ion exchange resin. The weak acid ion exchange resin consisted of the potassium salt of a cross-linked polymer of methacrylic acid and divinyl benzene commercially available as AMBERLITE IRP 88™. The resinate was divided into three parts and tested as follows:

24 mg of this resinate containing 15 mg codeine were subjected to testing in a standard dissolution apparatus according to USP 34 NF26 section 711. In one test, the pH was adjusted to 1.0 by 0.1 N HCl. In a second test, the pH was adjusted to 4.5 by means of buffers. The release of codeine from the resinate was measured at 15 minute intervals by high pressure liquid chromatography (HPLC).

Figure 2:
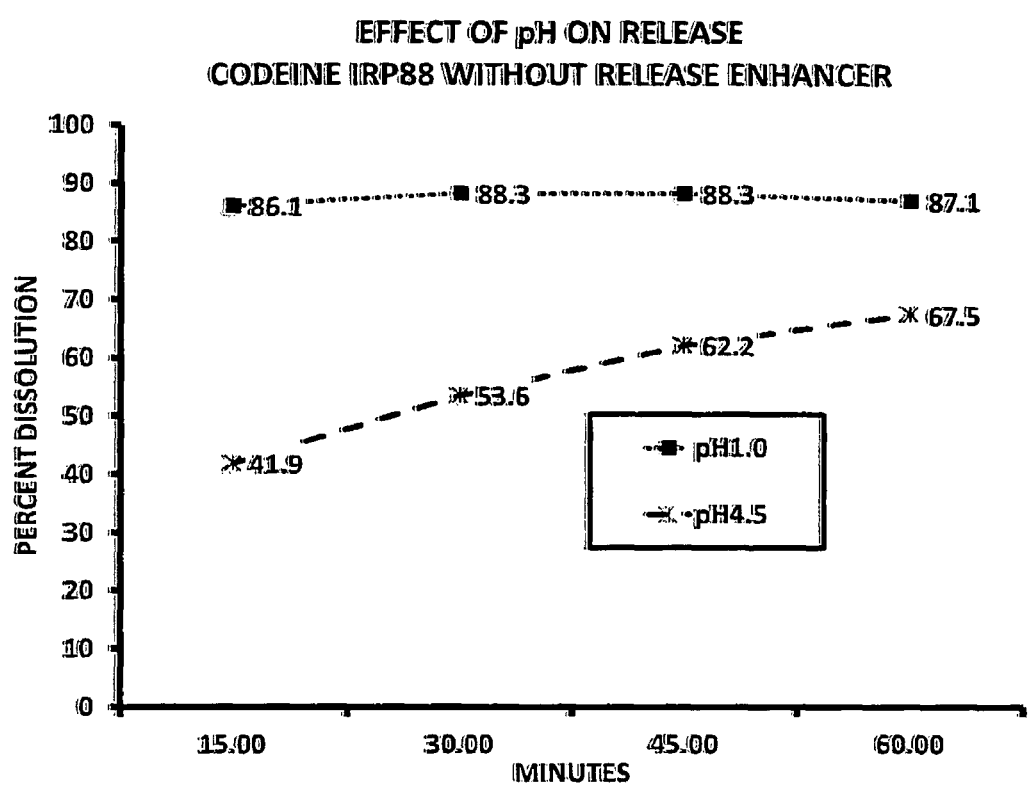
FIG. 2 shows the effect of pH on the release of codeine from a weak acid resinate in the absence of a release enhancer.

The resultant codeine release is tabulated below and is plotted in FIG. 2. It will be seen that the higher pH inhibited release of codeine from the resinate.

To a third 24 mg portion of the above described resinate containing 15 mg codeine was added 23.4 mg of $FeCl_3 \cdot 6H_2O$ (0.975 g/g resinate). The combined resinate and ferric chloride was subjected to testing in the same dissolution apparatus under the same conditions at a pH of 4.5 as above. The resultant codeine release is tabulated below and is plotted in FIG. 3.

Figure 3:
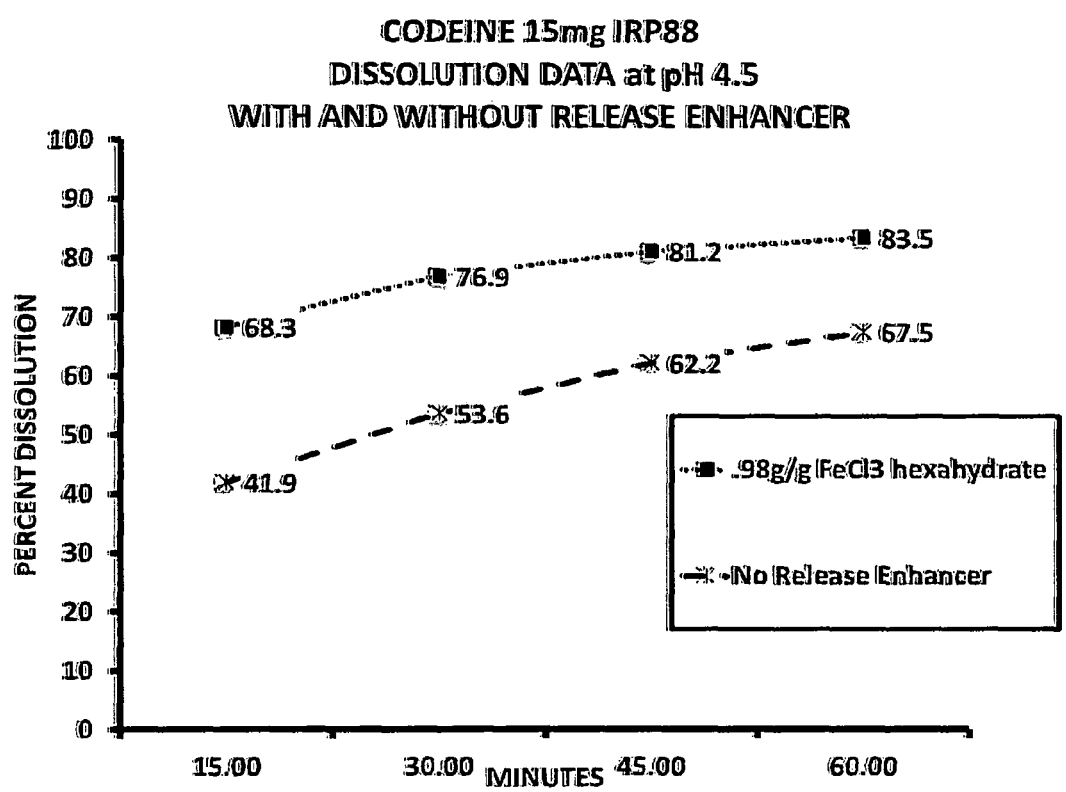
FIG. 3 shows dissolution of codeine weak acid resinate with and without a release enhancer.

It will be seen from the tabulated data and/or from FIG. 3 that the $Fe^{3+}$ acted as a release enhancing agent and caused a drug release in excess of 80% at 45 minutes where otherwise drug release was 62.2% without the release enhancer when a weak acid resinate was tested at pH 4.5.

TABLE 1

Dissolution Data for a Codeine Weak Acid Resinate at pH 1.0
Codeine Release From Codeine/IRP88 Resinate at 1.0 pH

| Dissolution time, min | Percent Release |
| --- | --- |
| 15 | 86.1 |
| 30 | 88.3 |
| 45 | 88.3 |
| 60 | 87.1 |

TABLE 2

Dissolution Data for a Codeine Weak Acid Resinate at pH 4.5
With And Without a Release Enhancer, $FeCl_3 \cdot 6H2O$
Codeine Release From Codeine/IRP88 Resinate at 4.5 pH

| | Percent Release | |
| --- | --- | --- |
| Dissolution time, min | Resinate Only | Resinate + $FeCl_3 \cdot 6H_2O$ |
| 15 | 41.9 | 68.3 |
| 30 | 53.6 | 76.9 |
| 45 | 62.2 | 81.2 |
| 60 | 67.5 | 83.5 |

Example 3

Example of a Tablet of the Invention Consisting of Three Distinct Layers

A resinate of hydrocodone bitartrate (HCBT) and the weak acid ion-exchange resin IRP88 was prepared by a process as in Example 1. The weak acid resinate had a drug to resin weight ratio of 1:2. This resinate was blended with FeCl3.6 H₂O to produce a mixture containing 0.975 gram FeCl3.6 H₂O per gram of resinate.

A resinate of HCBT and the strong acid ion-exchange resin IRP69 (sulfonated polyacrylic resin) was prepared by a process as in Example 1. The strong acid resinate had a drug to resin weight ratio of 1:2. This resinate was blended with anhydrous $CaCl_2$ to produce a mixture containing 0.208 grams of $CaCl_2$ per gram of resinate.

Pseudoephedrine HCL was mixed with 48 percent by weight of hydrogenated vegetable oil.

Figure 4:
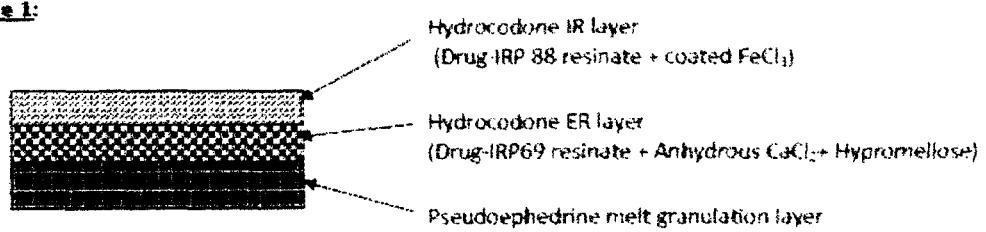
FIG. 4 is an illustration of a tablet of the invention consisting of three distinct layers.

The weak acid hydrocodone resinate, the strong acid hydrocodone resinate and the pseudoephedrine HCL were charged to separate hoppers on a tablet production machine. Compressed tablets were produced having the distinct layers as shown in the table below and illustrated schematically in FIG. 4. The tablets were capsule shaped standard convex having dimension of 19×7.6 mm.

| Layer | HCBT, mg | Ion-Exchange Resin, mg | $FeCl_3 \cdot 6H_2O$, mg | $CaCl_2$, mg | Pseudoephedrine HCL, mg |
| --- | --- | --- | --- | --- | --- |
| 1 (IR) | 2 | 4 | 5.85 | — | — |
| 2 (ER) | 8 | 16 | — | 5 | — |
| 3 | — | — | — | — | 120 |

Comparative Example 1

Weak Acid Resinate and Strong Acid Resinate in Same Layer

The weak acid hydrocodone resinate and the strong acid hydrocodone resinate described in Example 3 were blended together. The blended resinates and the pseudoephedrine HCL were charged to separate hoppers on a tablet production machine. Compressed tablets were produced having the distinct layers as shown in the table below.

| Layer | HCBT, mg | Ion-Exchange Resin, mg | $FeCl_3 \cdot 6H_2O$, mg | $CaCl_2$, mg | Pseudoephedrine HCL, mg |
| --- | --- | --- | --- | --- | --- |
| 1 | 10 | 20 | — | 15 | — |
| 2 | — | — | — | — | 120 |

Example 4

Dissolution of Example 3 and Comparative Example 1

Dissolution profiles of hydrocodone from the tablets of Example 3 and Comparative Example 1 were conducted in a standard dissolution apparatus according to USP31 NF 26 Section 711 at 50 RPM, 900 ml and paddle method in 0.1 N HCL.

Figure 5:
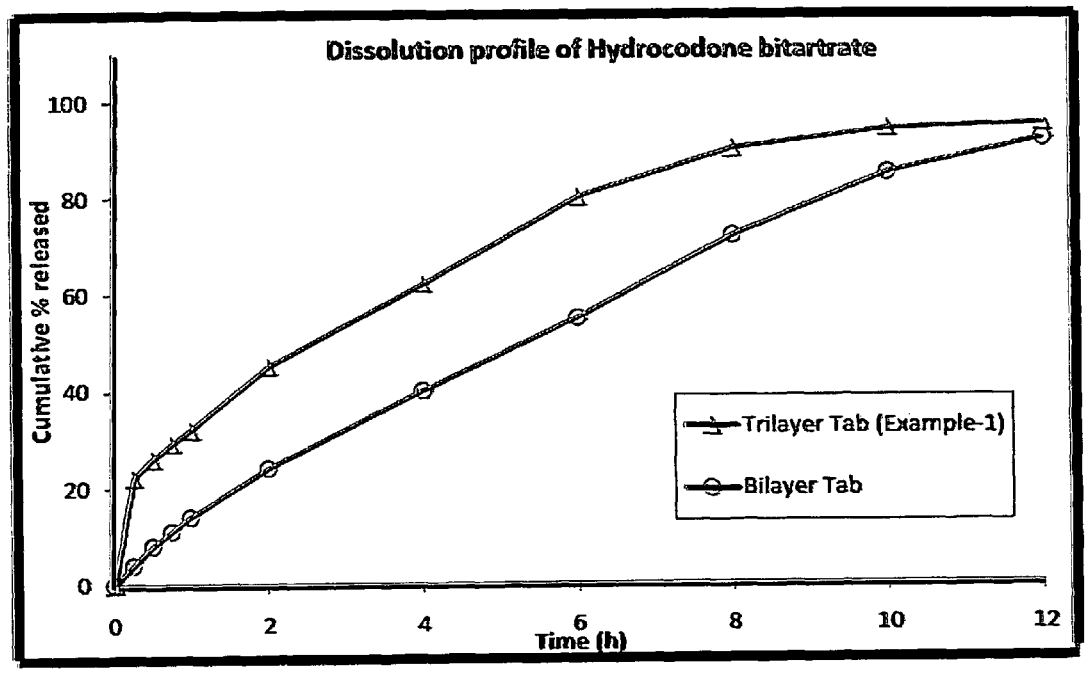
FIG. 5 shows the dissolution of hydrocodone bitartrate from a three layer tablet of the invention as illustrated in FIG. 4 wherein a weak acid resinate and a strong acid resinate are in separate and distinct layers compared to a two layer tablet in which the weak acid and the strong acid resinates are mixed together in the same layer.

The data are shown in FIG. 5. It will be seen that the dissolution of hydrocodone from the tri-layer tablet of the invention (Example 3) with separate weak acid and strong acid resinate layers was more rapid and more complete than from the bilayer tablet (Comparative Example 1) in which the weak acid and strong acid resinates were mixed.

Example 5

Figure 6:
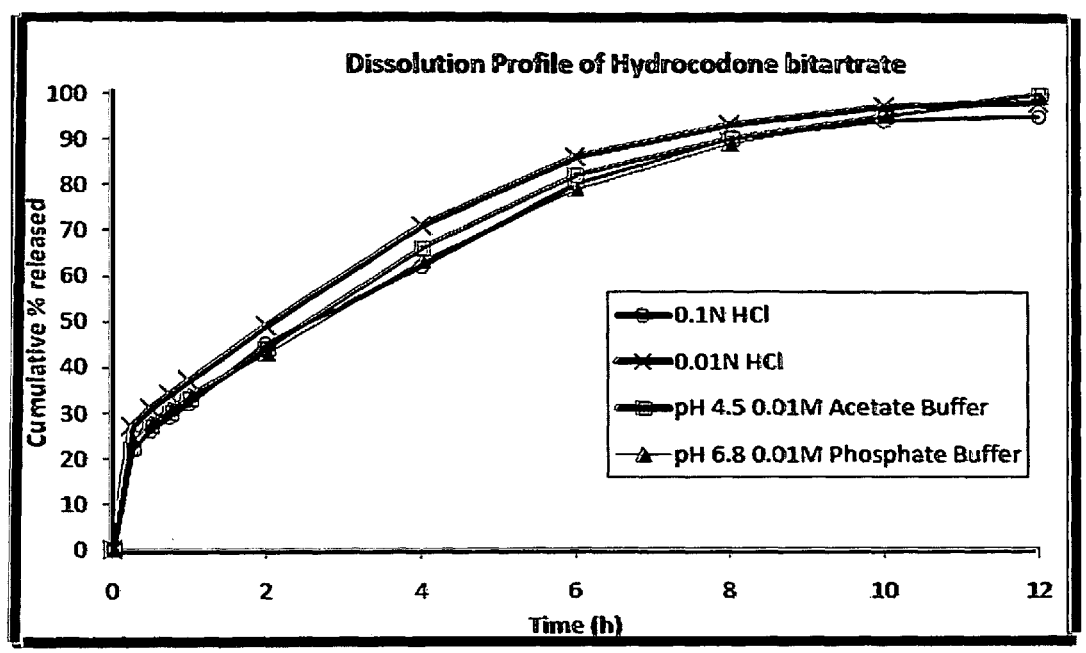
FIG. 6 shows the dissolution of hydrocodone bitartrate from a three layer tablet of the invention as a function of pH and time.
Figure 7:
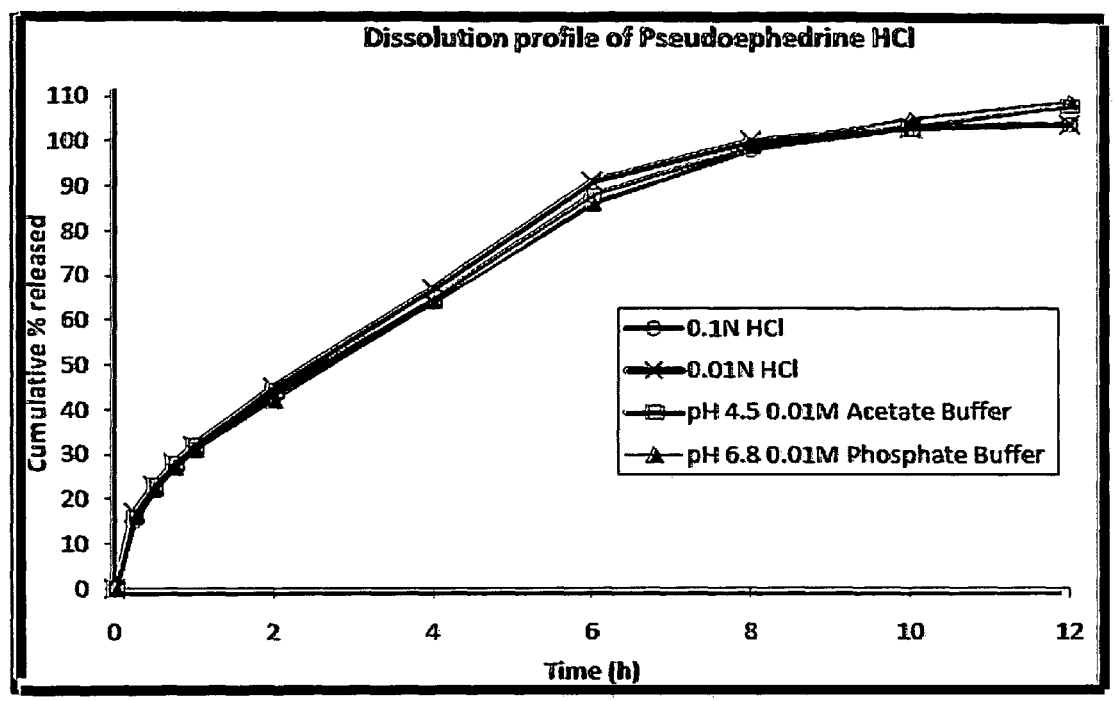
FIG. 7 shows the dissolution of pseudoephedrine HCl from a three layer tablet of the invention as a function of pH and time.

Dissolution profiles of the tablets of Example 3 were conducted in a standard dissolution apparatus according to USP31 NF 26 Section 711 at 50 RPM, 900 ml and paddle method. The studies were carried out in either 0.1 N HCL (pH1.2), 0.01 N HCl (pH 2.0), 0.01 M acetate buffer (pH 4.5) and 0.01 M phosphate buffer (pH 6.8). The dissolution profile of the hydrocodone as a function of pH is shown in FIG. 6. The dissolution profile of the pseudoephedrine HCl as a function of pH is shown in FIG. 7.

It will be seen that the dissolution profiles of the hydrocodone in the distinct layer structure of the composition of the invention were both rapid over the first 45 minutes and sustained for a period at least eight hours, even at pH greater than 1.5.

Figure 8:
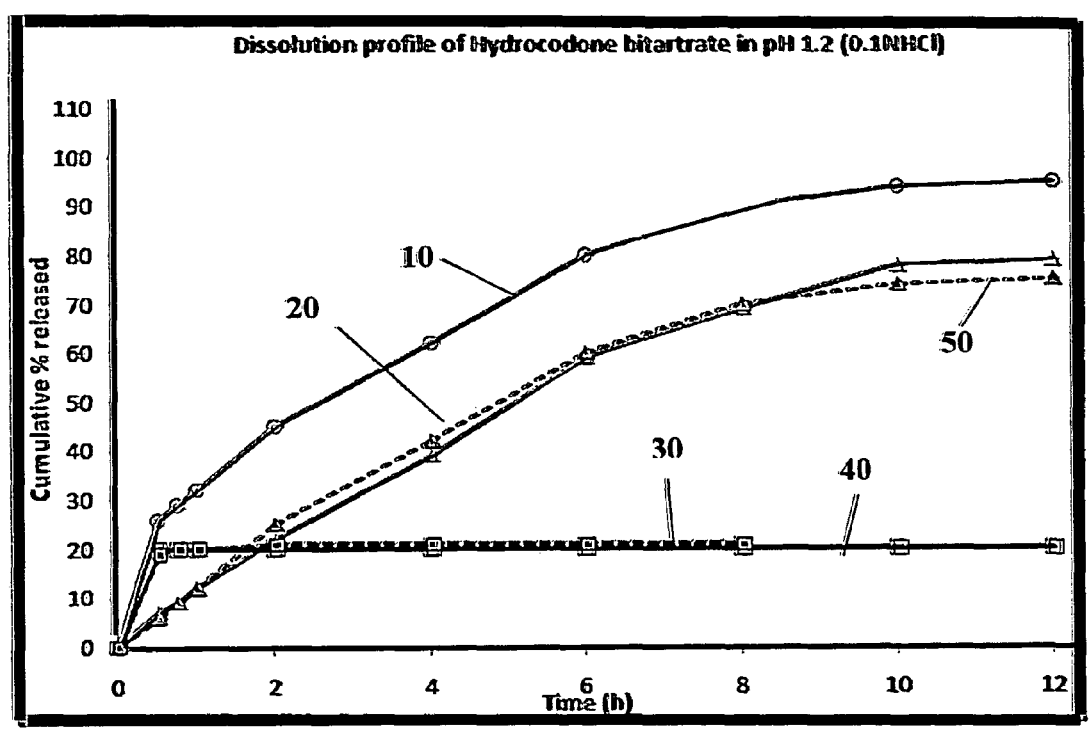
FIG. 8 shows the contributions of the immediate release and extended release components to the dissolution of hydrocodone bitartrate from a three layer tablet of the invention

FIG. 8 shows the contributions of the immediate release and extended release components to the dissolution of the hydrocodone from the tablets of Example 3 of the invention. In FIG. 8, the line 10 is the dissolution of the full composition of Example 3. The line 20 is the Example 3 structure with an inert filler instead of hydrocodone polacrilex in the "immediate release" layer. The line 30 is the contribution from the IR layer alone in Example 3.

The line 40 is the Example 3 structure with an inert filler instead of hydrocodone polistirex in the "extended release" layer. The line 50 is the contribution from the ER layer alone in Example 3.

It will be seen that that 20% of the total hydrocodone, essentially 100% of the hydrocodone in the immediate release, layer was released within the first 45 minutes.

Other Embodiments

All publications, patent applications, and patents mentioned in this specification are herein incorporated by reference.

Various modifications and variations of the described method and system of the invention will be apparent to those skilled in the art without departing from the scope and spirit of the invention. Although the invention has been described in connection with specific desired embodiments, it should be understood that the invention as claimed should not be unduly limited to such specific embodiments. Indeed, various modifications of the described modes for carrying out the invention that are obvious to those skilled in the fields of medicine, immunology, pharmacology, endocrinology, or related fields are intended to be within the scope of the invention.

What is claimed is:

1. A multi-layer solid oral pharmaceutical composition comprising;
   (i) a first distinct layer comprising:
      (a) a first pharmaceutically active agent bound to a weak acid ion exchange resin to form a weak acid ion-exchange resinate; and
      (b) a release-enhancing agent consisting of $FeCl_3$;
   (ii.) at least a second distinct layer comprising:
      (a) a drug selected from the group consisting of said first pharmaceutically active agent and a second pharmaceutically active agent, said drug being bound to a strong acid ion exchange resin to form a strong acid ion-exchange resinate; and
      (b) optionally, a coating to slow and extend release of the drug contained therein;
   wherein said pharmaceutical composition is capable of immediate release of said first pharmaceutically active agent from said weak acid resinate at a pH of at least 1.5, immediate release being defined as at least 80% release of said pharmaceutically active agent within 45 minutes in a standard dissolution apparatus according to USP 34 NF 26 section 711; and, wherein release of the drug from said strong acid resinate continues over a period of at least 8 hours after ingestion.

2. The multi-layer solid oral pharmaceutical composition of claim 1 having at least three distinct layers, each said layer comprising pharmaceutically active agents in a form selected from the group consisting of ion-exchange resinates and unbound pharmaceutically active agents.

3. The multi-layer solid oral pharmaceutical composition of claim 1 where said first layer comprises a member of the group consisting of hydrocodone bitartrate polacrilex weak acid resinate, codeine polacrilex weak acid resinate and dextromethorphan polacrilex weak acid resinate; and said second layer comprises a member of the group consisting of hydrocodone polistirex strong acid resinate, codeine polistirex strong acid resinate and dextromethorphan polistirex strong acid resinate.

4. The multi-layer solid oral pharmaceutical composition of claim 2, wherein, at least one of said layers comprises an unbound pharmaceutically active agent.

5. The multi-layer solid oral pharmaceutical composition of claim 4 wherein said first layer comprises a member of the group consisting of hydrocodone bitartrate polacrilex weak acid resinate, codeine polacrilex weak acid resinate and dextromethorphan polacrilex weak acid resinate; and said second layer comprises a member of the group consisting of hydrocodone polistirex strong acid resinate, codeine polistirex strong acid resinate and dextromethorphan polistirex strong acid resinate; and
   wherein a third layer consists of an unbound pharmaceutically active agent.

6. A method of treating a patient with a stomach pH of at least about 1.5 comprising administration of a multilayer solid oral dosage form said dosage form comprising:
   (i) a first distinct layer comprising:
      (a) a first pharmaceutically active agent bound to a weak acid ion exchange resin to form a weak acid ion-exchange resinate; and
      (b) a release-enhancing agent selected from the group consisting of an inorganic salt and an organic base;
   (ii.) at least a second distinct layer comprising:
      (a) a drug selected from the group consisting of said first pharmaceutically active agent and a second pharmaceutically active agent, said drug being bound to a strong acid ion exchange resin to form a strong acid ion-exchange resinate; and,
      (b) optionally, a coating to slow and extend release of the drug contained therein;
   wherein said pharmaceutical composition is capable of immediate release of said first pharmaceutically active agent from said weak acid resinate at a pH of at least 1.5, immediate release being defined as at least 80% release of said pharmaceutically active agent within 45 minutes in a standard dissolution apparatus according to USP 34 NF 26 section 711; and, wherein release of the drug from said strong acid resinate continues over a period of at least 8 hours after ingestion.

7. A method of treating a patient having a first condition and a second condition with a pharmaceutically active agent effective for treating said second condition, said method comprising the step of administering a solid oral dosage pharmaceutical composition, said solid oral dosage pharmaceutical composition comprising:
   (i) a first distinct layer comprising:
      (a) a first pharmaceutically active agent bound to a weak acid ion exchange resin to form a weak acid ion-exchange resinate; and,
      (b) a release-enhancing agent selected from the group consisting of an inorganic salt and an organic base;

(ii.) at least a second distinct layer comprising:
(a) pharmaceutically active agent selected from the group consisting of said first pharmaceutically active agent and a second pharmaceutically active agent, said pharmaceutically active agent bound to a strong acid ion exchange resin to form a strong acid ion-exchange resinate; and,
(b) optionally, a coating to slow and extend release of the drug contained therein;

wherein said pharmaceutical composition is capable of immediate release of said first pharmaceutically active agent from said weak acid resinate at a pH of at least 1.5, immediate release being defined as at least 80% release of said pharmaceutically active agent within 45 minutes in a standard dissolution apparatus according to USP 34 NF 26 section 711; and, wherein release of the drug from said strong acid resinate continues over a period of at least 8 hours after ingestion; and wherein said first condition is selected from the group consisting of *Helicobacter pylori* infection, atrophic gastritis, hypochlorhydria and achlorhydria in the stomach; and wherein said second condition is a condition other than said first condition.

8. A method of treating a patient wherein the patient has within the past 24 hours been administered a compound selected from the group consisting of a proton pump inhibitor, an H2 receptor antagonist, and an antacid, said method comprising the step of administering a solid oral dosage pharmaceutical composition, said solid oral dosage pharmaceutical composition comprising:
(i) a first distinct layer comprising:
(a) a first pharmaceutically active agent bound to a weak acid ion exchange resin to form a weak acid ion-exchange resinate; and;
(b) a release-enhancing agent selected from the group consisting of an inorganic salt and an organic base;
(ii.) at least a second distinct layer comprising:
(a) pharmaceutically active agent selected from the group consisting of said first pharmaceutically active agent and a second pharmaceutically active agent, said pharmaceutically active agent bound to a strong acid ion exchange resin to form a strong acid ion-exchange resinate, and
(b) optionally, a coating to slow and extend release of the drug contained therein;

wherein said pharmaceutical composition is capable of immediate release of said first pharmaceutically active agent from said weak acid resinate at a pH of at least 1.5, immediate release being defined as at least 80% release of said pharmaceutically active agent within 45 minutes in a standard dissolution apparatus according to USP 34 NF 26 section 711; and, wherein release of the drug from said strong acid resinate continues over a period of at least 8 hours after ingestion.

9. A method of delivering a pharmaceutically active agent to a patient, said method comprising orally administering a solid oral dosage composition comprising:
(i) a first distinct layer comprising:
(a) a first pharmaceutically active agent bound to a weak acid ion exchange resin to form a weak acid ion-exchange resinate; and
(b) a release-enhancing agent selected from the group consisting of an inorganic salt and an organic base;
(ii.) at least a second distinct layer comprising:
(a) pharmaceutically active agent selected from the group consisting of said first pharmaceutically active agent and a second pharmaceutically active agent, said pharmaceutically active agent bound to a strong acid ion exchange resin to form a strong acid ion-exchange resinate; and,
(b) optionally, a coating to slow and extend release of the drug contained therein;

wherein said pharmaceutical composition is capable of immediate release of said first pharmaceutically active agent from said weak acid resinate at a pH of at least 1.5, immediate release being defined as at least 80% release of said pharmaceutically active agent within 45 minutes in a standard dissolution apparatus according to USP 34 NF 26 section 711; and, wherein release of the drug from said strong acid resinate continues over a period of at least 8 hours after ingestion.

* * * * *